(12) United States Patent
Paulus

(10) Patent No.: US 7,182,596 B2
(45) Date of Patent: Feb. 27, 2007

(54) ORTHODONTIC DEVICE

(75) Inventor: Werner Paulus, Burgbernheim (DE)

(73) Assignee: Bredent Dentalgerate und Materialien Fach-und Organisationsberatung Peter Brehm, Senden (DE)

(*) Notice: Subject to any disclaimer, the term of this patent is extended or adjusted under 35 U.S.C. 154(b) by 78 days.

(21) Appl. No.: 10/129,429

(22) PCT Filed: Feb. 27, 2001

(86) PCT No.: PCT/DE01/00724

§ 371 (c)(1),
(2), (4) Date: Jul. 26, 2004

(87) PCT Pub. No.: WO01/64126

PCT Pub. Date: Sep. 7, 2001

(65) Prior Publication Data

US 2005/0084815 A1  Apr. 21, 2005

(30) Foreign Application Priority Data

Feb. 29, 2000 (DE) .................. 200 03 634 U

(51) Int. Cl.
*A61C 3/00* (2006.01)
(52) U.S. Cl. .................. 433/6; 433/18; 433/21

(58) Field of Classification Search ........ 433/6–7, 433/18, 21, 24
See application file for complete search history.

(56) References Cited

U.S. PATENT DOCUMENTS

| | | | | |
|---|---|---|---|---|
| 3,574,941 A * | 4/1971 | Ritter | ........ | 433/18 |
| 3,827,146 A * | 8/1974 | Wallshien | ........ | 433/7 |
| 3,975,825 A * | 8/1976 | Smith | ........ | 433/7 |
| 4,054,996 A * | 10/1977 | Wallshein | ........ | 433/7 |
| 4,370,129 A * | 1/1983 | Huge | ........ | 433/6 |
| 4,609,349 A * | 9/1986 | Cain | ........ | 433/6 |
| 4,793,803 A * | 12/1988 | Martz | ........ | 433/6 |
| 4,799,884 A * | 1/1989 | Bergersen | ........ | 433/6 |
| 5,145,364 A * | 9/1992 | Martz et al. | ........ | 433/6 |
| 5,328,362 A * | 7/1994 | Watson et al. | ........ | 433/6 |
| 5,580,243 A * | 12/1996 | Bloore | ........ | 433/6 |

FOREIGN PATENT DOCUMENTS

| | | |
|---|---|---|
| DE | 4020647 A1 * | 1/1992 |
| FR | 1456601 * | 10/1966 |

\* cited by examiner

*Primary Examiner*—John J Wilson
(74) *Attorney, Agent, or Firm*—Andrew Wilford

(57) ABSTRACT

The invention comprises a jaw orthopedic device for the movement and/or correction of teeth in the tooth arch with a synthetic resin element and/or at least one mature element or tooth contacting or tooth movement, whereby the synthetic resin element is comprised of a hard synthetic resin material and the synthetic resin element (1) has at least one soft plastic element (3) integrated therewith for tooth contacting or tooth movement.

13 Claims, 1 Drawing Sheet

[//]: #

ORTHODONTIC DEVICE

CROSS REFERENCE TO RELATED APPLICATIONS

This application is the US national phase of PCT application PCT/DE01/00724, filed 27 Feb. 2001, published 7 Sep. 2001 as WO 01/64126, and claiming the priority of German patent application 20003634.3 itself filed 29 Feb. 2000.

FIELD OF THE INVENTION

The invention relates to a jaw orthodontic device for the movement and/or correction of teeth where the tooth arch has a synthetic resin element and/or at least one wire element for tooth contacting or tooth movement.

BACKGROUND OF THE INVENTION

As the state of the art, colloquially also known as tooth correction, jaw orthodontic devices are known which have, apart from hard synthetic resin materials and wire elements, springs or screws for tooth contacting. Tooth movement is possible with such springs or screws only in a limited manner. The locations of attack of the springs or screws are effective by limited points and the respective effective forces can be controlled only to a limited degree. In addition, such jaw orthodontic devices with springs or screws, because of their bulky construction, can only be accommodated uncomfortably in the mouth space.

OBJECT OF THE INVENTION

The invention has as its object the provision of a jaw orthodontic device for movement or correction of teeth which, for example, affords improved possibilities for effecting tooth movement.

The object is achieved in that the synthetic resin element has at least one soft plastic element integrated therein for tooth contacting or tooth movement.

Via the soft plastic element permanently applied and integrated in the synthetic resin element of the jaw orthodontic device according to the invention, new possibilities of tooth contacting and tooth movement are afforded by comparison with the state of the art. By contrast with conventional jaw orthodontic devices with springs or screws, integrated soft plastic elements enable a yieldable contacting of the respective tooth or plurality of teeth, whereby the effective force can be uniformly and thus more pleasantly applied to the teeth.

The synthetic resin element can be composed of various hard synthetic resin materials, for example of methylmethacrylate or polymethylmethacrylate which are known per se from prior jaw orthodontic appliances.

The soft plastic element can be composed especially of silicone material, for example, of vinylpolysiloxane. In sum, the jaw orthodontic device according to the invention enables regions of the synthetic resin element to be equipped with conventional hard synthetic resin material when a guide and anchoring of the jaw orthodontic device is desired. In those regions of the tooth arch in which individual teeth or groups of teeth are to be moved and newly positioned, soft plastic elements can be used which are integrated in and bonded permanently with the hard plastic material (e.g. cross-linked or adhesively bonded) so that the synthetic resin element is configured as a two-component or multi-component unit.

Because of the use of soft plastic elements, tooth movements can be achieved which are controllable in a targeted manner and a number of variations are enabled like, for example, intrusion, extrusion or rotation. Especially it is possible above all in the front tooth region for the soft plastic element to engage around the teeth and thereby transmit a tensile stress to the teeth.

The soft plastic element can also be used in fields in which no tooth movement is to be achieved but rather only an especially comfortable guidance for anchoring of the jaw orthodontic appliance is desired.

The soft plastic element can be effective especially for intrusion or extrusion of a tooth on the respective attachment which is to be applied to the particular tooth. As an additional point or as an alternative, a flat contact of the soft element with the tooth can be produced in order to distribute the forces which may arise over large areas of the tooth.

In addition or alternatively, the jaw orthodontic device according to the invention can also be provided with conventional springs or screws which are either effective directly on the tooth in the conventional way or bear upon the tooth indirectly in that the springs or the screws initially act upon that plastic element which then conducts the pressure to the tooth or the teeth.

According to a further advantageous embodiment, the jaw orthodontic device of the invention can also have local synthetic resin elements of different hard synthetic resin materials.

To obtain the desired pressure distribution or pressing forces, for example in different regions of the tooth arch, the soft plastic elements can also be integrated locally and can include different materials or be of different thicknesses and/or different dimensions.

According to a further embodiment, at least one wire element can be incorporated in the yieldable jaw orthodontic appliance according to the invention or in a soft plastic element. The wire element can be incorporated in another application also on a synthetic resin element.

As a whole, through alternative anchoring points of the wire element on the synthetic resin or soft plastic element, desirable loading forces for the tooth arch can be controllable and metered out with precision.

BRIEF DESCRIPTION OF THE DRAWING

The invention is described in greater detail in conjunction with exemplary embodiments in the drawing Figures. They show.

SPECIFIC DESCRIPTION

Figure 1:
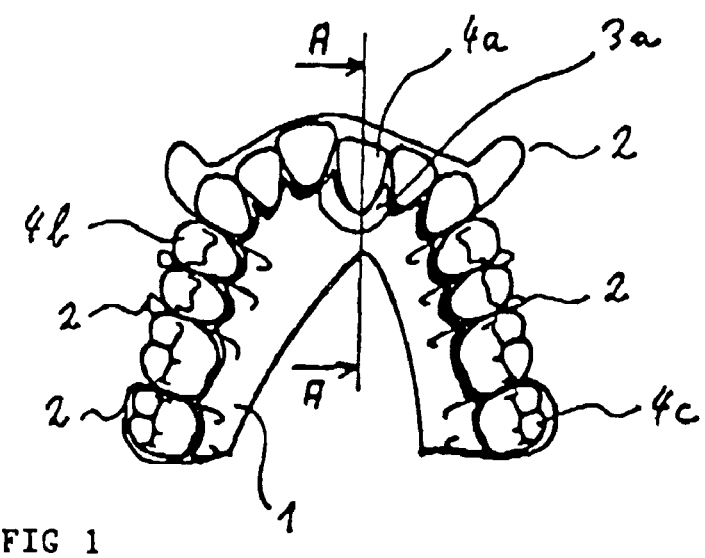
FIG. 1 a schematic illustration of a jaw with a jaw orthodontic appliance set in place before the desired tooth movement, FIG. 2 an illustration of the jaw with the jaw orthodontic appliance set in place after the desired tooth movement as well as FIG. 3 a section A—A according to FIG. 1.

From FIG. 1 a schematic illustration of the jaw (tooth arch) can be seen, with a tooth 4$a$ which is for example dislocated and is to be repositioned in the tooth arch through the use of the jaw orthodontic appliance (for example as a dental brace). The jaw orthodontic appliance is comprised of a removable synthetic resin element 1 with wire elements 2 which engage through and around teeth 4$b$ and 4$c$ for guiding and anchoring.

Figure 2:
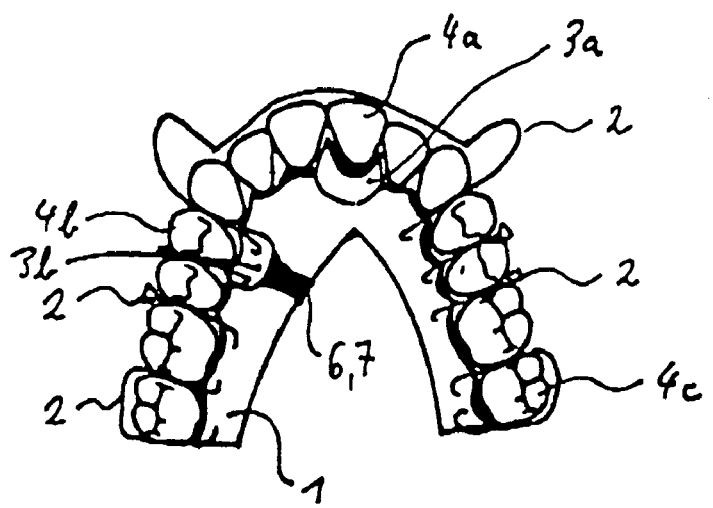

In the region of the tooth 4a, a soft plastic element 3a is integrated in the synthetic resin element 1 with a permanent connection and contacts the tooth 4a in order to apply a continuous pressure from the jaw orthodontic appliance to move it into its outwardly shifted position according to FIG. 2.

FIG. 2 shows a jaw orthodontic appliance with a synthetic resin element 1 and a first soft plastic element 3a which bears upon the tooth 4a and a further soft plastic element 3b which bears upon the tooth 4b. Behind the soft plastic element 3b a schematically shown spring 6 or screw 7 is incorporated which is effective against the tooth 4b via the soft plastic element 3b. By means of the intervening action of the soft plastic element 3b, the pressure of the spring 6 or the screw 7 can be applied to the tooth 4b with damping and in a measured manner.

Figure 3:

According to the sectional illustration of FIG. 3, the soft plastic element 3a, which is permanently bonded with the synthetic resin element 1, acts upon an additional element 5 applied to the tooth 4a and upon the latter so that it applies pressure to the latter by way of intrusion in the direction 8. In the case of an extrusion, the soft plastic element 3 can engage beneath the additional element 5. Furthermore, the soft plastic element 3 can also engage around the additional element 5, for example, to effect a rotation (not illustrated).

In summary, the jaw orthodontic appliance of the invention can be locally configured and detailed so that for each individual tooth of the tooth arch, a respective engagement can be achieved whether by a region of hard synthetic resin material or an integrated soft plastic element 3 with or without backup stress by means of a spring 6 or a screw 7.

The invention claimed is:

1. An orthodontic device for correcting a position of a tooth in an arch of teeth, the device comprising:
    a hard synthetic-resin element shaped to fit in the arch;
    a soft plastic element yieldingly engageable with the tooth whose position is to be corrected so as to apply a uniform force to the tooth; and
    a screw engaged between the hard element and the soft element for pressing the soft element against the tooth and thereby correcting the position thereof.

2. The jaw orthodontic device according to claim 1, wherein the hard element is comprised of methylmethacrylate or polymethylmethacrylate.

3. The jaw orthodontic device according to claim 1, wherein the soft plastic element is comprised of a silicone material.

4. The jaw orthodontic device according to claim 1, wherein the soft plastic element matches a contour the tooth to be corrected.

5. The jaw orthodontic device according to claim 1, further comprising
    an additional element on the tooth to be corrected, the soft plastic element contacting the additional element of the tooth for extrusion, intrusion or rotation of the tooth to be corrected.

6. The jaw orthodontic device according to claims 1, wherein the soft plastic element in use contacts flat against the tooth to be corrected.

7. The jaw orthodontic device according to claim 1, further comprising
    at least one spring for tooth contacting and bracing between the hard element and a tooth to be corrected.

8. The jaw orthodontic device according to claim 7, wherein the spring in use directly contacts the tooth to be corrected.

9. The jaw orthodontic device according to claim 7, wherein the spring in use contacts the tooth to be corrected indirectly via an additional soft plastic element.

10. The jaw orthodontic device according to claim 1, wherein the synthetic resin element is composed of locally different hard synthetic resin materials.

11. The jaw orthodontic device according to claim 1, wherein a plurality of such soft plastic elements of different materials is provided.

12. The jaw orthodontic device according to claim 1, further comprising
    at least one wire element incorporated in the soft plastic element.

13. The jaw orthodontic device according to claim 1, further comprising
    at least one wire element incorporated in the synthetic resin element and in an additional soft plastic element.

* * * * *